US007726262B2

(12) United States Patent
Stampe et al.

(10) Patent No.: US 7,726,262 B2
(45) Date of Patent: Jun. 1, 2010

(54) DEVICE AND SYSTEM FOR PREVENTING ANIMAL WOUND LICKING

(75) Inventors: David A. Stampe, Crosslake, MN (US); Kay C. Stampe, Crosslake, MN (US)

(73) Assignee: Discoveries 180, Inc., Crosslake, MN (US)

( * ) Notice: Subject to any disclaimer, the term of this patent is extended or adjusted under 35 U.S.C. 154(b) by 165 days.

(21) Appl. No.: 12/028,453

(22) Filed: Feb. 8, 2008

(65) Prior Publication Data

US 2008/0190381 A1 Aug. 14, 2008

Related U.S. Application Data

(60) Provisional application No. 60/888,773, filed on Feb. 8, 2007.

(51) Int. Cl.
*A01K 13/00* (2006.01)
*A61M 35/00* (2006.01)

(52) U.S. Cl. ....................... 119/850; 119/860; 604/309; 606/48; 424/411

(58) Field of Classification Search ................. 119/850, 119/650, 652–654, 856, 860, 857, 655, 672; 604/308, 309; 43/136, 114; 602/48, 41–59, 602/304–308; 424/411; 239/36; 54/79.4, 54/79.1
See application file for complete search history.

(56) References Cited

U.S. PATENT DOCUMENTS

| | | | | |
|---|---|---|---|---|
| 2,066,946 | A | 1/1937 | Reiman | |
| 2,209,914 | A | 7/1940 | Gerber | |
| 2,342,066 | A * | 2/1944 | Tramill | 119/654 |
| 2,401,253 | A * | 5/1946 | Lamb, Jr. | 119/654 |
| 2,634,229 | A | 4/1953 | Roux de Wet | |
| 2,734,483 | A * | 2/1956 | Peo | 119/654 |
| 2,791,202 | A * | 5/1957 | Doyle | 119/654 |
| 3,339,546 | A | 9/1967 | Chew | |
| 3,580,254 | A | 5/1971 | Stuart | |
| 3,996,934 | A | 12/1976 | Zaffaroni | |
| 4,097,607 | A | 6/1978 | Larson | |
| 4,184,452 | A * | 1/1980 | Buzzell et al. | 119/654 |

(Continued)

FOREIGN PATENT DOCUMENTS

JP 09205975 8/1997

(Continued)

OTHER PUBLICATIONS

Insect Treatments, Jan. 23, 1999, retrieved from internet: Nov. 4, 2009.*

(Continued)

*Primary Examiner*—Rob Swiatek
*Assistant Examiner*—Kristen C Hayes
(74) *Attorney, Agent, or Firm*—Dovas Law, P.C.

(57) ABSTRACT

A device for application on an animal for deterring the animal from wound licking is provided. The device includes a flexible first layer of material and a deterrent composition in contact with the flexible first layer of material. A layer of adhesive is connected with the flexible first layer of material, and a second layer of material is connected with the layer of adhesive opposite the flexible first layer of material. A method for deterring an animal from licking a wound is also provided.

17 Claims, 5 Drawing Sheets

U.S. PATENT DOCUMENTS

| | | | | |
|---|---|---|---|---|
| 4,671,960 | A * | 6/1987 | Thielen et al. | 424/405 |
| 4,804,142 | A * | 2/1989 | Riley | 239/56 |
| 4,879,117 | A * | 11/1989 | Rombi | 424/411 |
| 4,900,876 | A * | 2/1990 | Bushman et al. | 119/654 |
| 4,901,674 | A * | 2/1990 | Bushman et al. | 119/651 |
| 4,930,451 | A * | 6/1990 | Miller et al. | 119/654 |
| 5,035,893 | A | 7/1991 | Shioya et al. | |
| 5,254,338 | A | 10/1993 | Sakai et al. | |
| 5,455,043 | A * | 10/1995 | Fischel-Ghodsian | 424/448 |
| 5,476,492 | A | 12/1995 | Unrug | |
| 5,896,830 | A | 4/1999 | Stampe | |
| D417,529 | S | 12/1999 | Stampe | |
| 6,070,557 | A | 6/2000 | Hibbert | |
| 6,165,514 | A | 12/2000 | Bockman et al. | |
| 6,197,325 | B1 | 3/2001 | MacPhee et al. | |
| 6,274,555 | B1 | 8/2001 | Berdami | |
| 6,362,388 | B1 | 3/2002 | Lucas | |
| 6,453,850 | B1 | 9/2002 | Stampe | |
| 6,468,554 | B1 | 10/2002 | Ichino | |
| 6,967,261 | B1 | 11/2005 | Soerens et al. | |
| 7,011,843 | B2 | 3/2006 | Becher et al. | |
| 7,185,613 | B2 * | 3/2007 | Arvanitis | 119/860 |
| 7,287,489 | B1 | 10/2007 | O'Brien | |
| 7,380,370 | B2 * | 6/2008 | Livingston | 43/124 |
| 2003/0175332 | A1 | 9/2003 | Brown et al. | |
| 2004/0185088 | A1 | 9/2004 | Pearson et al. | |
| 2004/0185115 | A1 | 9/2004 | Pearson et al. | |
| 2005/0048859 | A1 | 3/2005 | Canham et al. | |
| 2005/0214351 | A1 | 9/2005 | Chen | |
| 2005/0284419 | A1 * | 12/2005 | Bazar | 119/856 |
| 2009/0246241 | A1 * | 10/2009 | Pitt | 424/410 |

FOREIGN PATENT DOCUMENTS

| | | |
|---|---|---|
| WO | WO96/28113 | 9/1996 |
| WO | WO 9956548 A1 * | 11/1999 |

OTHER PUBLICATIONS

FrappyDoo online discussion forum, Jan. 11, 2001 through Feb. 8, 2001; http://www.frappydoo.com/forum/archive/index.php/t-953.html.

Puotinen. C.J. Accelerated wound healing: help your dog heal quickly and cleanly with these gentle. natural methods. Whole Dog Journal, Aug. 1, 2006, pp. 1-7, p. 3, para 2.

David Stampe, Discoveries 180, Inc., Press release, Dec. 10, 2007.

* cited by examiner

DEVICE AND SYSTEM FOR PREVENTING ANIMAL WOUND LICKING

BACKGROUND

Many animals including pets and livestock have an instinctual urge to lick wounds. Licking wounds may be effective in limited circumstances to help with the wound healing process. Enzymes in an animals mouth can help keep a wound clean and potentially disinfect a wound. However, it is generally accepted in the veterinary community that with the advent of modern disinfectants and antibiotics wound licking by an animal is in most cases detrimental, since the mechanical process of licking tends to prolong the healing process risking later infection. In cases of surgeries in particular, wound licking by an animal may be especially injurious. Moreover, an animal's habitual licking of its skin may lead to a serious skin disorder such as Acral Lick Granulomas or Acral Lick Dermatitis. In the worst cases, animals classified as "obsessive habitual lickers" may aggressively continue to a lick a wound to such extent that limb amputation is required or the animal's life is lost.

Special collars have been attached to certain animals to prevent them from seeing and reaching a wound. However, such devices are awkward and frequently limit an animal's visibility, potentially endangering the animal. Moreover, it is not practical to use such collars on all types of animals. Various sprays and lotions have also been developed to be applied near a wound to discourage animal licking. However, these compositions are easily removed and may actually encourage animal licking by triggering an animal's instinctual urge to clean its body of foreign substances.

It would be desirable to provide a simple and practical device or method for preventing wound licking by animals which can be implemented easily on many different types of animals.

SUMMARY

The present invention provides a device for application on an animal for deterring the animal from wound licking. The device includes a flexible first layer of material and a deterrent composition in contact with the flexible first layer of material. A layer of adhesive is connected with the flexible first layer of material, and a second layer of material is connected with the layer of adhesive opposite the flexible first layer of material.

The present invention also provides a method for deterring an animal from licking a wound. The method includes providing a device including a flexible first layer of material, a deterrent composition with at least one odor causing constituent in contact with the flexible first layer, a layer of adhesive connected with the flexible first layer of material, and a second layer of material connected with the adhesive opposite the flexible first layer of material. The second layer of material is removed to expose the adhesive. The device is attached to an animal using the adhesive, and the animal is permitted to inhale volatile constituents of the deterrent composition.

The present invention further provides a method for deterring an animal from licking a wound in which a device is provided with a flexible permeable membrane and at least one deterrent composition including particulate solids covered by and in contact with the flexible permeable membrane. In this method the device is adhered to an animal using an adhesive.

BRIEF DESCRIPTION OF THE DRAWING(S)

The foregoing Summary as well as the following detailed description will be readily understood in conjunction with the appended drawings which illustrate preferred embodiments of the invention. In the drawings.

DETAILED DESCRIPTION OF THE PREFERRED EMBODIMENT(S)

Figure 1:
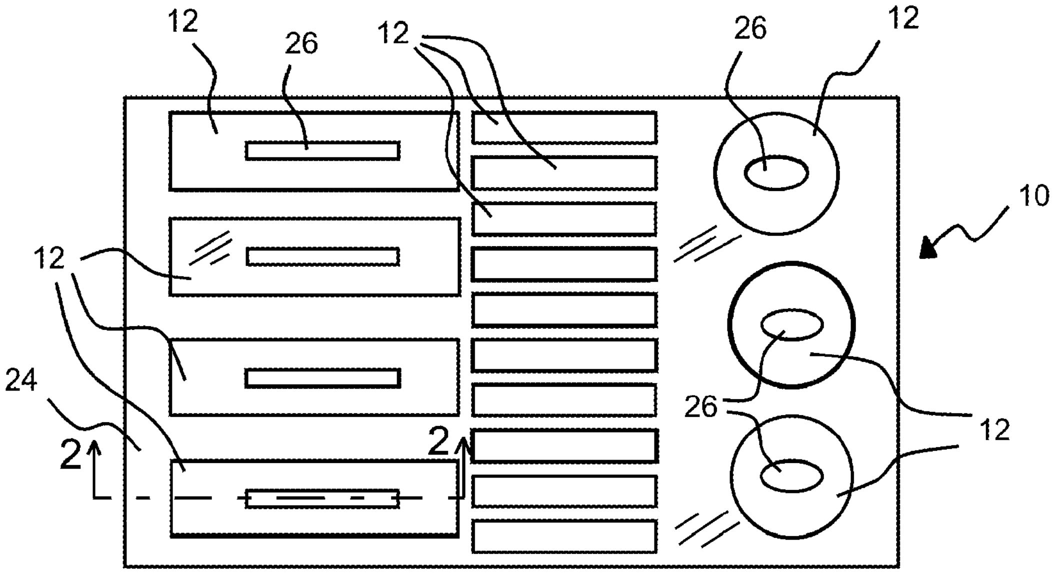
FIG. 1 is a top plan view of a dispensing sheet including a plurality of lick deterrent devices according to a first preferred embodiment of the present invention.

Certain terminology is used in the following description for convenience only and is not limiting. The words "right," "left," "top," and "bottom" designate directions in the drawings to which reference is made. The words "a" and "one" are defined as including one or more of the referenced item unless specifically stated otherwise. This terminology includes the words above specifically mentioned, derivatives thereof, and words of similar import. The phrase "at least one" followed by a list of two or more items, such as A, B, or C, means any individual one of A, B or C as well as any combination thereof.

The preferred embodiments of the present invention are described below with reference to the drawing figures where like numerals represent like elements throughout.

Figure 2:
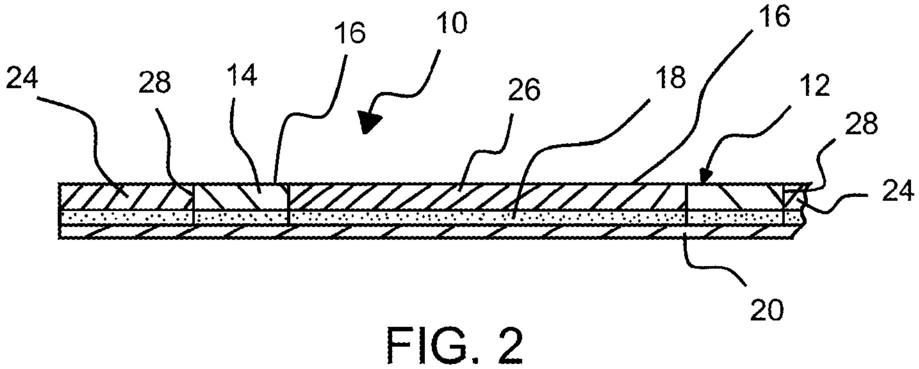
FIG. 2 is a partial section view of the dispensing sheet of FIG. 1 through line 2-2 of FIG. 1.

Referring to FIGS. 1 and 2, a deterrent device dispensing sheet 10 including a plurality of lick deterrent devices 12 according to a first preferred embodiment of the present invention is shown. The lick deterrent devices 12 include a composition layer 14 having a lick deterrent composition 16 disposed thereon. An adhesive 18 is affixed to a surface of the composition layer 14 opposite the deterrent composition 16. Preferably, a release liner 20 shared by each of the lick deterrent devices 12 is removably attached to the adhesive 18. The lick deterrent devices 12 are separable from their release liner 20 exposing the adhesive 18 on the composition layer 14 to allow adhering of the deterrent device 12 to an animal, for example in proximity to an animal's wound. Waste portions 24 of the composition layers 14 remain attached to the release liner 20 when the lick deterrent devices 12 are separated from their release liner 20. Alternatively, the deterrent device 12 may be provided without an adhesive or release liner, and an adhesive may be applied prior to affixing the deterrent device 12 to an animal.

At least some of the deterrent devices 12 preferably include removable portions 26 which may be removed by a user if desired to permit the deterrent device 12 to be adhered directly over an animal's wound, with the wound and any wound sutures remaining exposed through an aperture created by removing a removable portion 26. Accordingly, the deterrent device 12 may be easily attached on or in close proximity to an animal's wound to discourage the animal from licking the wound, while leaving the wound exposed to air to promote healing.

Figure 3:
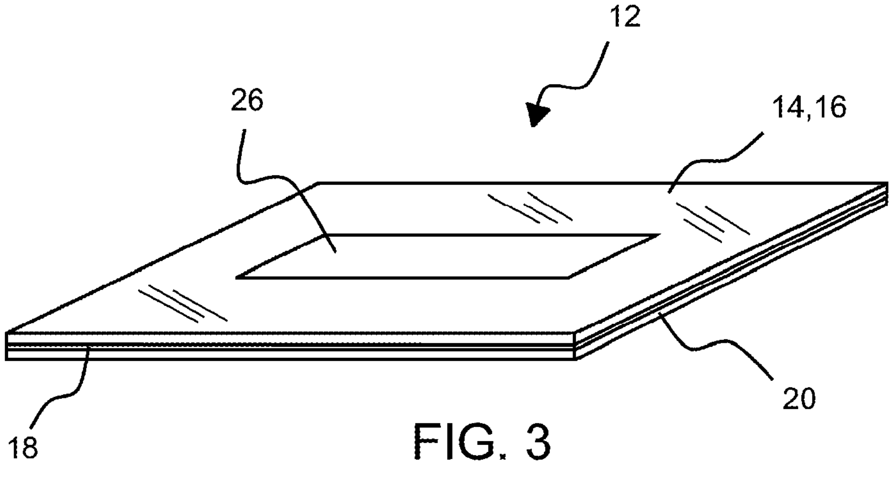
FIG. 3 is a perspective view of an individually provided lick deterrent device according to the first preferred embodiment of the present invention.

Die cuts 28 separate the plurality of deterrent devices 12 into various forms as shown. Alternatively, the dispensing sheet 10 can be provided without die cuts to allow a user to cut deterrent devices 12 from the dispensing sheet in any desired form to suit a particular application. Alternatively, as shown in FIG. 3, the deterrent device 12 can be provided individually with its own release liner 20, which is not shared with other deterrent devices.

The composition layer 14 preferably includes a flexible breathable polymeric material suitable for retaining the deterrent composition 16 thereon. Such polymeric material may include for example nylon or Ultrex®. Alternatively, the composition layer 14 may include a fabric material, a paper material, or any material suitable for retaining the deterrent composition 16 thereon.

The deterrent composition 16 preferably includes a composition which emits a strong odor to discourage an animal from licking an area where the deterrent device 12 is applied. Such deterrent composition 16 preferably includes natural or synthetic menthol. Alternatively, the deterrent composition 16 may include other odor causing constituents including but not limited to pepper, salts, ammonia, bitter principles, and natural or synthetic lemon. In addition to or in place of odor causing constituents, the deterrent composition 16 preferably includes a constituent with an objectionable taste to further discourage animal licking. The objectionable tasting constituent preferably includes citrullus colocynthus to produce a bitter apple or bitter cucumber taste. Alternatively, the deterrent composition 16 may include other objectionable tasting constituents including but not limited to pepper, salts, ammonia, bitter principles, and natural or synthetic lemon.

The deterrent composition 16 is preferably disposed as a thin layer on an outer surface of the composition layer 14, as shown. Alternatively, the deterrent composition 16 may be formed integrally with the composition layer 14. As one preferred example, the deterrent composition 16 may be mixed with a rubber base used to form the composition layer 14. In such case, the deterrent composition 16 may be completely homogeneously mixed with the rubber base or disposed at or near a surface of the composition layer 14 after a rubber curing process. As another preferred example, the deterrent composition 16 may be absorbed by a composition layer 14 which includes paper or fabric material.

Figure 4:
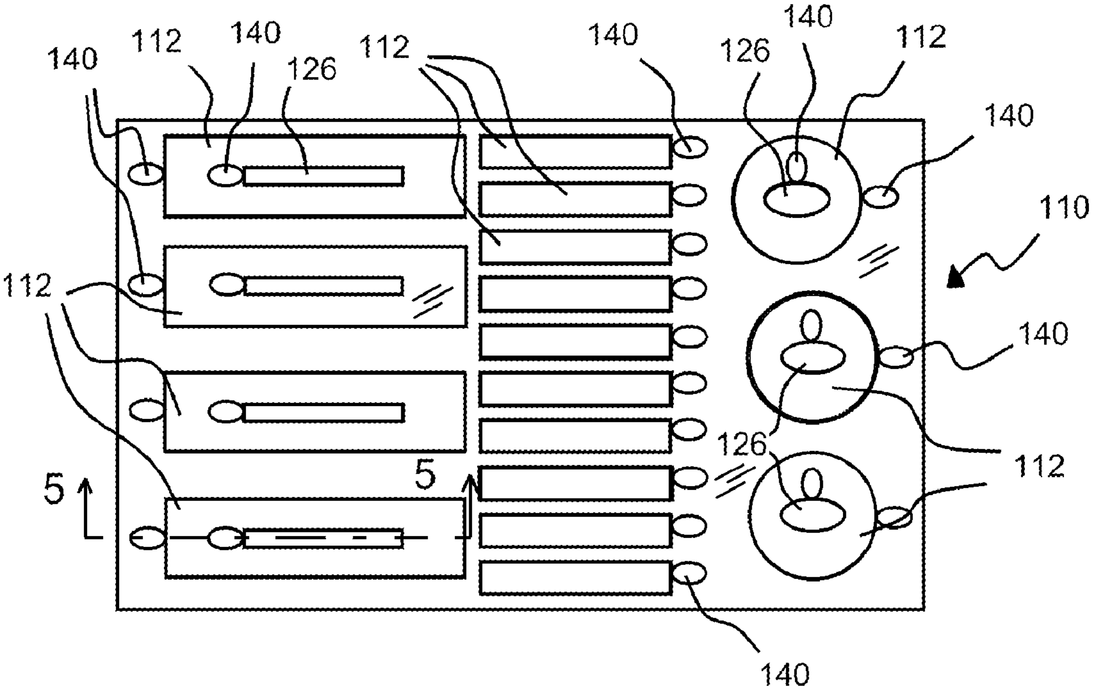
FIG. 4 is a top plan view of a dispensing sheet including a plurality of lick deterrent devices with peel tabs according to a second preferred embodiment of the present invention.
Figure 5:
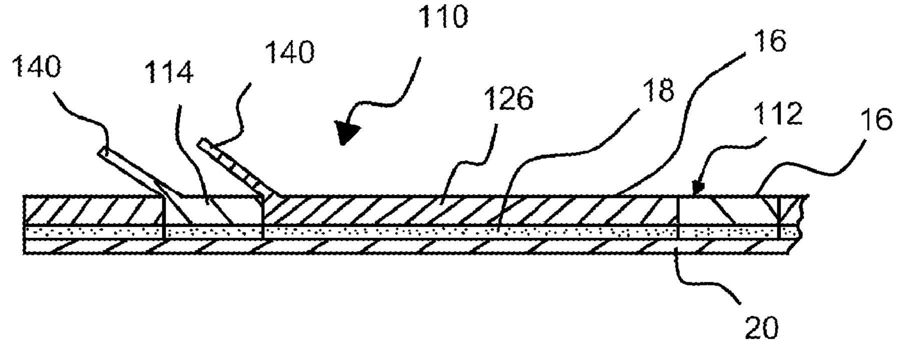
FIG. 5 is a partial section view of the dispensing sheet of FIG. 1 through line 5-5 of FIG. 4.

Referring to FIGS. 4 and 5, a dispensing sheet 110 including a plurality of deterrent devices 112 according to a second preferred embodiment of the present invention is shown. The dispensing sheet 110 is similar to the dispensing sheet 10, but further includes peel tabs 140 attached to each of the plurality of deterrent devices 112 on a composition layer 114 to facilitate their removal from the release liner 20. Peel tabs 140 are also provided on removable portions 126 of the deterrent devices 112.

Figure 6:
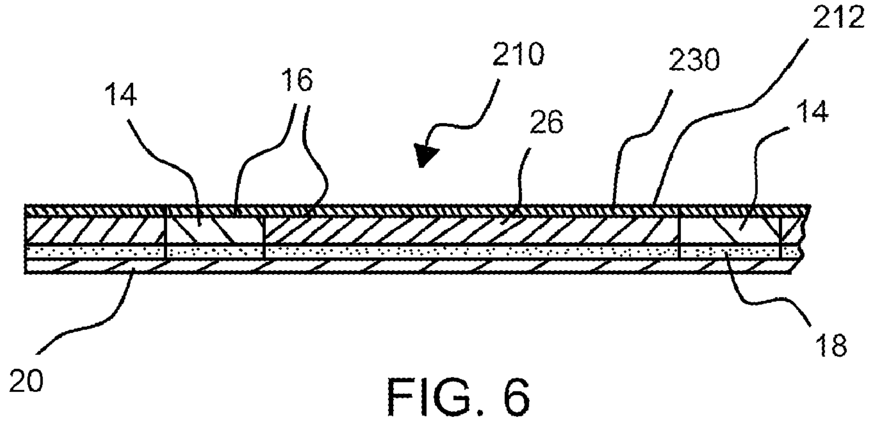
FIG. 6 is a partial side section view of a dispensing sheet including a plurality of lick deterrent devices with a permeable membrane according to a third preferred embodiment of the present invention.

Referring to FIG. 6, a dispensing sheet 210 including a plurality of deterrent devices 212 according to a third preferred embodiment of the present invention is shown. The dispensing sheet 210 is similar to the dispensing sheet 10, but further includes a permeable membrane 230 connected to the composition layer 14 over the deterrent composition 16. Since certain deterrent compositions 16 may be harmful to an animal if ingested, the permeable membrane 230 allows objectionable vapors to be released while preventing harmful chemicals, or significant quantities of harmful chemicals, from passing through to prevent ingestion by an animal which licks the device 212. Alternatively, the permeable membrane 230 may be configured to permit a metered amount of deterrent composition 16 to pass through to an outer surface thereof such that an animal can be exposed to an objectionable taste and/or odor, but will not ingest a significant amount of the deterrent composition 16.

Figure 7:
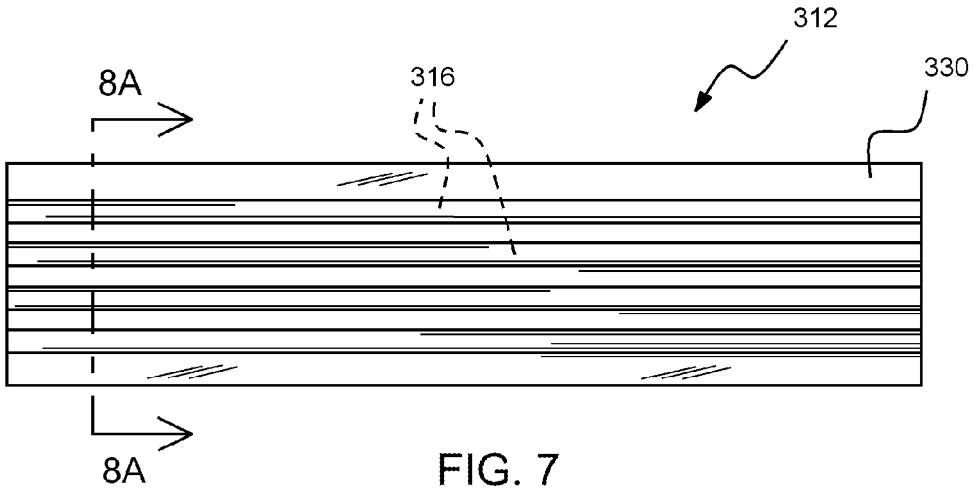
FIG. 7 is a top plan view of a lick deterrent device a according to a fourth preferred embodiment of the present invention.
Figure 8A:
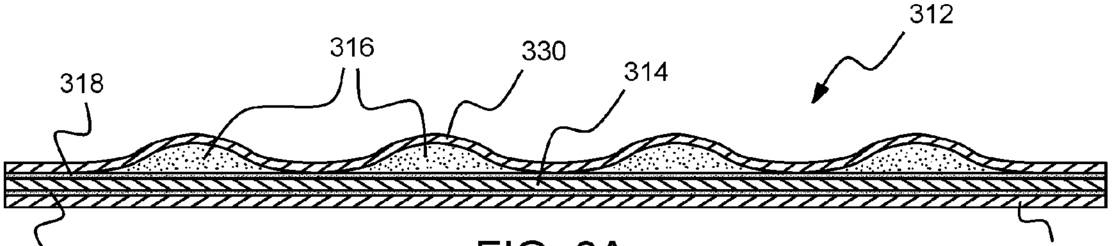
FIG. 8A is a section view of the lick deterrent device of FIG. 7 through line 8A-8A of FIG. 7.
Figure 8B:
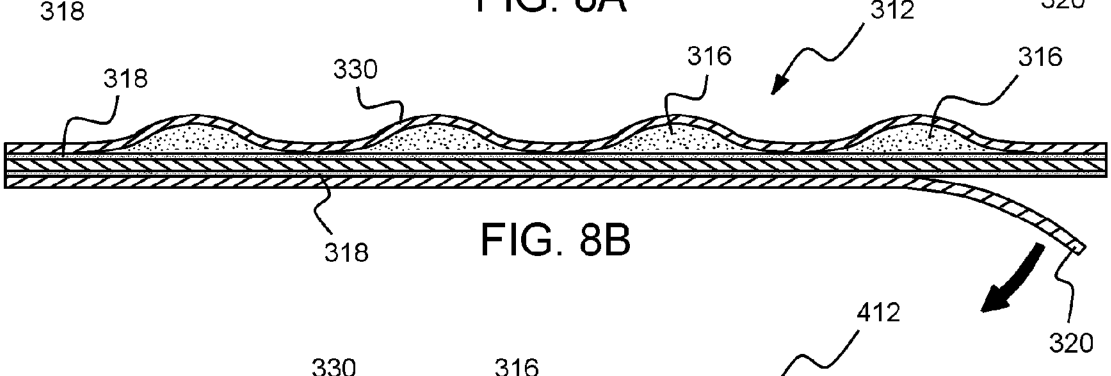
FIG. 8B is a section view of the lick deterrent device of FIG. 7 showing partial removal of a release liner.
Figure 10:
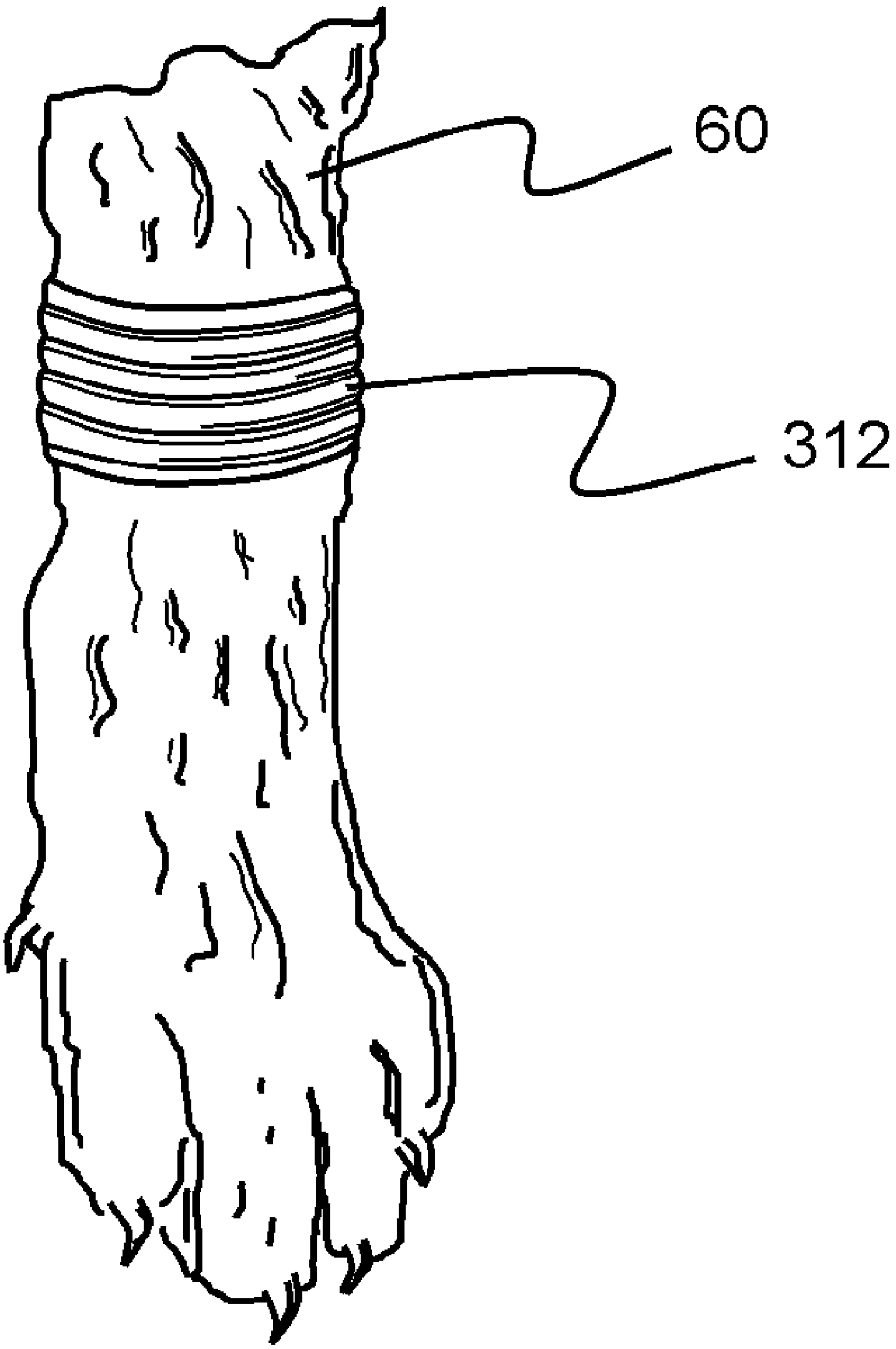
FIG. 10 is a partial front view of a dog leg and the lick deterrent device of FIG. 7 attached thereto.

Referring to FIGS. 7, 8A and 8B, a lick deterrent device 312 according to a fourth preferred embodiment of the present invention is shown. The lick deterrent device 312 includes a carrier layer 314 on which an adhesive 318 is disposed on two opposing sides thereof. A deterrent composition 316 is adhered to the carrier layer 314 by a first layer of the adhesive 318. A permeable membrane 330 over the deterrent composition 316 is adhered to the carrier layer 314 by the first layer of the adhesive 318. A release liner 320 is removably adhered to the carrier layer 314 by a second layer of the adhesive 318. Once the release liner 320 is removed in the manner shown in FIG. 8B, the device 312 may be adhered to an animal via the second layer of the adhesive 318, for example to the leg of an animal 60 in the manner shown in FIG. 10. The carrier layer 314 may prevent the deterrent composition 316 from contacting the fur or skin of an animal on which the device 312 is adhered.

The deterrent composition 316 is preferably in particulate form having particle size less than 2 mm and more preferably having particle size less than 800 μm (powdered). The deterrent composition 316 preferably includes cayenne pepper powder, oregano powder, and lemon powder. The cayenne pepper powder is preferably 100,000 BTU cayenne pepper powder, or alternatively, other type of cayenne pepper powder of suitable spiciness, but preferably rated not higher than 100,000 BTU using the accepted spiciness rating system known in the trade. The deterrent composition 316 preferably includes equal parts cayenne pepper powder and oregano powder by mass, and approximately ten percent lemon powder by mass. Alternatively any suitable proportion of ingredients may be used. Further, other non-toxic strong tasting or strong smelling constituents can alternatively be used for the deterrent composition 316.

While not wishing to be limited by the constituents' theorized functionality, the powdered cayenne pepper, oregano and lemon are each useful for providing taste and smell considered objectionable to an animal. The lemon powder is further useful as a caking agent to prevent an excessive amount of the powdered cayenne pepper and oregano from passing through the permeable membrane 330 in dried form, although as indicated below, a limited amount of the deterrent composition 316 may pass through the permeable membrane 330 in dried form.

The permeable membrane 330 can include synthetic or natural fabric. The permeable membrane 330 is preferably organza, which is an open weave woven material. The organza is preferably configured with weave openings of size suitable to permit a limited amount of the deterrent composition 316 to pass through in solid form. The organza is preferably provided with another deterrent composition including an odor causing composition applied thereto and integral therewith. Preferably, the odor causing composition includes clove extract soaked into fibers of the organza. The clove extract may be provided as clove oil in an acetone-based solvent or other suitable solvent applied to the organza, which is thereafter evaporated prior to assembly of the device 312, such that solvent is not present in the assembled device 312. The permeable membrane 330 may alternatively be formed from any suitable permeable material, woven or non-woven, with any suitable odor causing composition applied thereto. The device 312 is preferably packaged in an airtight sleeve to prevent release of volatile constituents, including volatile constituents of the odor causing composition, prior to use of the device 312.

While not wishing to be limited by any particular theory of functionality, when the device 312 is licked, an animal's saliva will pass through pores of the permeable membrane 330 creating a liquid solution with the deterrent composition 316. The liquid solution, including saliva and the deterrent composition 316, passes back through the pores of the permeable membrane 330 and is consumed by the animal, with the volatile constituents of the solution being inhaled by the animal. The taste and scent of the deterrent composition 316 are generally objectionable to an animal, so the animal may be discouraged from continued licking.

Prior to licking, the animal may inhale volatile constituents of the odor causing composition, and to lesser extent, volatile constituents of the dry deterrent composition 316 which pass through the permeable membrane 330. Without licking, a small portion of the deterrent composition 316 in powdered form may pass through pores of the permeable membrane 330, such that an animal inhaling in close proximity to the lick deterrent device 312 may further inhale the solid particles of the deterrent composition 316. The inhalation of the solid and volatile constituents of the deterrent composition 316 is typically objectionable, although not typically harmful, to an animal and may cause sneezing or other response indicating the animal's objection. Accordingly, an animal may come to associate the displeasing taste of the deterrent composition 316 with the smell of the volatile constituents of the deterrent composition 316 including the odor causing composition. This association may assist with training the animal to stop undesirable licking behavior as discussed further below.

The carrier layer 314 is preferably formed of a thin polymer material which is substantially impermeable with respect to the deterrent composition 316 under normal use. More preferably, the carrier layer 314 and the two layers of adhesive 318 are integrally provided as a double-sided adhesive film, wherein during the assembly of the lick deterrent device 312, a first layer of the adhesive 318 is exposed to the deterrent composition 316 and the permeable membrane 330. The adhesive 318 is preferably an acrylic adhesive. Alternatively, any suitable adhesive including a rubber adhesive may be used.

The lick deterrent device 312 may be provided individually as shown in FIG. 7 and suitably sized, preferably 1.5" by 5", for application on a household pet. Alternatively, the lick deterrent device 312 may be provided in any suitable size or shape. Further, the lick deterrent device 312 may be provided as a single long length on a perforated or un-perforated roll to permit a user to cut a desired length of the device 312 as required by a particular application.

Figure 9A:
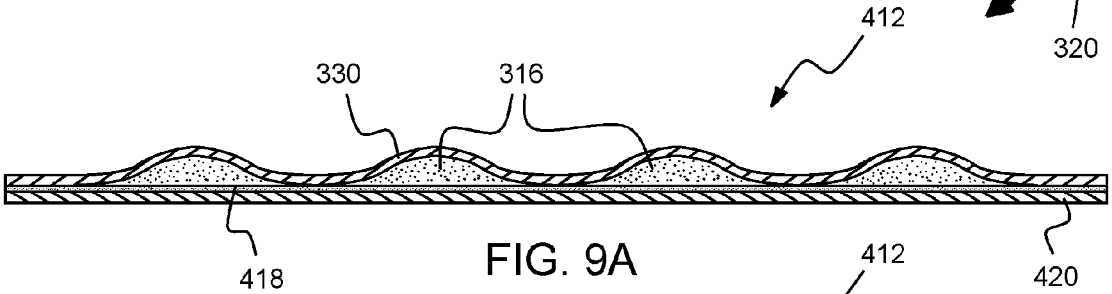
FIG. 9A is a section view of a lick deterrent device according to a fifth preferred embodiment of the present invention.
Figure 9B:
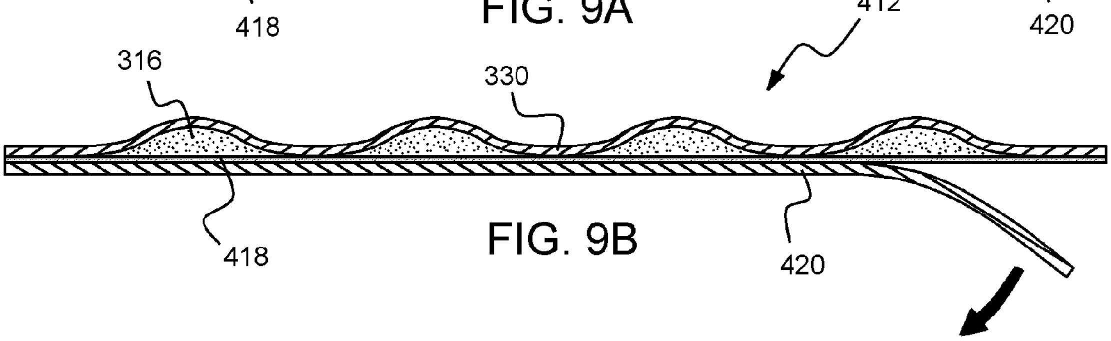
FIG. 9B is a section view of the lick deterrent device of FIG. 9A showing partial removal of a release liner.

Referring to FIGS. 9A and 9B, a lick deterrent device 412 according to a fifth preferred embodiment of the present invention is shown in which the deterrent composition 316 and the permeable membrane 330 are adhered to a removable release liner 420 via an adhesive 418. Once the release liner 420 is removed in the manner shown in FIG. 9B, the device 412 may be adhered to an animal via the adhesive 418. The adhesive 418 further functions to retain the deterrent composition 316 against the permeable membrane 330. It is preferred that the device 412 be used over a wound dressing or other suitable barrier on an animal's skin or fur, since only the adhesive 418 separates the deterrent composition 412 from a surface on which it is attached. Such wound dressing or other barrier may prevent the deterrent composition 316 from coming in contact with the skin or fur of an animal on which the deterrent device 412 is adhered.

Each of the deterrent devices 12, 112, 212, 312, 412 may be applied directly to an animal's fur or skin, or alternatively, over an animal's wound dressing, for example a dressing including a gauze pad or hydrocolloid pad and medication or ointment. When applied securely over an animal's wound dressing, the deterrent devices 12, 112, 212, 312, 412 may provide the additional functionality of preventing the animal from disassembling the dressing.

While not wishing to be limited by any particular theory of functionality of the devices 12, 112, 212, 312, 412, an animal may be discouraged from licking by the objectionable odor or the objectionable taste of the deterrent compositions 16, 316. In a case in which the deterrent composition 16, 316 is provided with constituents having both objectionable taste and objectionable odor, or in the case in which an additional odor causing composition is provided with the device, an animal which tastes the objectionable taste constituent may make a mental association between the objectionable taste and the objectionable odor, even if the odor is not particularly objectionable to the animal. Further, after associating the odor with the objectionable taste resulting from licking behavior, the animal may at a later time be discouraged from licking by the objectionable odor alone, without necessitating any actual licking of a lick deterrent device, and in some cases if desired, without necessitating application of a lick deterrent device directly onto the animal. Moreover, since the compositions 16, 316 are incorporated into respective devices 12, 112, 212, 312, 412 and not applied to an animal's body directly, an animal's cleaning instinct may not be triggered, and the animal is less likely to persist in trying to remove the composition 16, 316.

The deterrent devices 12, 112, 212, 312, 412 are effective in preventing wound licking, including habitual wound licking, on any suitable animals, for example domesticated dogs, cats, and horses. The deterrent devices 12, 112, 212, 312, 412 may also be applied to other surfaces, for example furniture, fence posts and gates, to discourage other undesirable oral habits such as horse cribbing.

Figure 11:
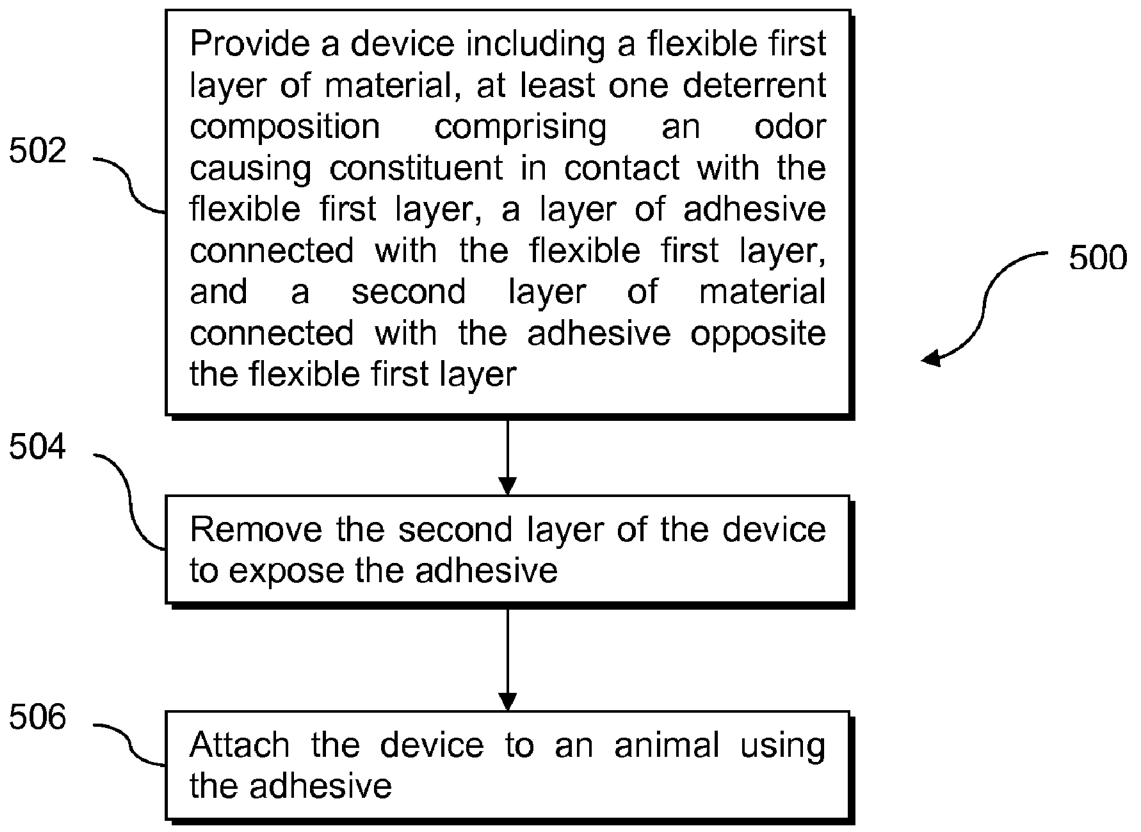
FIG. 11 is a flow chart showing a method for deterring an animal from licking a wound according to a preferred embodiment of the present invention.

Referring to FIG. 11, a method 500 for deterring an animal from licking a wound according to a preferred embodiment of the present invention is shown. The method 500 includes providing a device including a flexible first layer of material, at least one deterrent composition comprising an odor causing constituent in contact with the flexible first layer, a layer of adhesive connected with the flexible first layer, and a second layer of material connected with the adhesive opposite the flexible first layer (step 502). The second layer of the device is removed to expose the adhesive (step 504). The device is attached to an animal using the adhesive (step 506).

While the preferred embodiments of the invention have been described in detail above, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. A device for application on an animal for deterring the animal from wound licking, the device comprising:
- a flexible first layer of material comprising a solids-permeable membrane;
- a layer of adhesive connected with the flexible first layer of material;
- a second layer of material connected with the layer of adhesive opposite the flexible first layer of material; and
- at least one deterrent composition in contact with the solids-permeable membrane comprising particulate solids which are positioned between the solids-permeable membrane and the second layer of material, wherein at least a portion of the particulate solids are sized to pass through the solids-permeable membrane, and wherein the particulate solids comprise dried cayenne pepper, dried oregano, and dried lemon.

2. A device for application on an animal for deterring the animal from wound licking, the device comprising:
- a flexible first layer of material comprising a solids-permeable membrane comprising at least one of a synthetic and natural open weave fabric;
- a layer of adhesive connected with the flexible first layer of material;
- a second layer of material connected with the layer of adhesive opposite the flexible first layer of material; and
- at least one deterrent composition in contact with the solids-permeable membrane comprising particulate solids which are positioned between the solids-permeable membrane and the second layer of material, wherein at least a portion of the particulate solids are sized to pass through the solids-permeable membrane.

3. The device of claim 2, wherein the at least one deterrent composition is positioned between the layer of adhesive and the solids-permeable membrane, and the at least one deterrent composition is in contact with the layer of adhesive.

4. The device of claim 2, wherein the particulate solids are grouped in rows and the first layer of material is connected to the second layer of material via the adhesive in areas formed between the rows of grouped particulate solids.

5. The device of claim 2, wherein the particulate solids comprise at least one of dried cayenne pepper, dried oregano, and dried lemon.

6. The device of claim 2, wherein the particulate solids are sized less than about 800 μm in width.

7. The device of claim 2, wherein the solids-permeable membrane comprises organza.

8. The device of claim 2, wherein the second layer of material is removably connected to the layer of adhesive for exposing the layer of adhesive, whereby the device may be adhered to a surface using the layer of adhesive.

9. The device of claim 8, wherein a first side of the layer of adhesive is adhered to the at least one deterrent composition and the first layer of material, and a second side of the layer of adhesive is adhered to the second layer of material.

10. The device of claim 2, further comprising another deterrent composition, wherein the another deterrent composition comprises an odor causing composition applied to the solids-permeable membrane.

11. The device of claim 2, further comprising another deterrent composition, wherein the another deterrent composition comprises clove extract.

12. A device for application on an animal for deterring the animal from wound licking, the device comprising:
- a flexible first layer of material comprising a solids-permeable membrane;
- a layer of adhesive connected with the flexible first layer of material;
- a second layer of material removably connected to the layer of adhesive opposite the flexible first layer of material for exposing the layer of adhesive, whereby the device may be adhered to a surface using the layer of adhesive;
- at least one deterrent composition in contact with the solids-permeable membrane comprising particulate solids which are positioned between the solids-permeable membrane and the second layer of material, wherein at least a portion of the particulate solids are sized to pass through the solids-permeable membrane; and
- a substantially impermeable third layer of material between the first layer of material and the second layer of material connected to the layer of adhesive on a first side and connected to the first layer of material on a second side opposite the first side.

13. The device of claim 12, wherein the third layer of material is adhered to the first layer of material and the at least one deterrent composition by another layer of adhesive.

14. A method for deterring an animal from licking a wound, the method comprising:
- providing a device comprising a flexible solids-permeable first layer of material, at least one deterrent composition comprising odor causing particulate solids in contact with the flexible solids-permeable first layer of material, an adhesive connected with the flexible solids-permeable first layer of material, and a second layer of material connected with the adhesive opposite the flexible solids-permeable first layer of material;
- removing the second layer of material to expose the adhesive;
- attaching the device to an animal using the adhesive; and
- permitting the animal to inhale the particulate solids and odors thereof through the flexible solids-permeable first layer of material.

15. The method of claim 14, further comprising attaching the device to the animal at least one of over a wound and adjacent to a wound of the animal.

16. A method for deterring an animal from licking a wound, the method comprising:
- providing a device comprising a flexible solids-permeable membrane and at least one deterrent composition which comprises particulate solids covered by and in contact with the flexible solids-permeable membrane, wherein at least a portion of the particulate solids are sized to pass through the solids-permeable membrane;
- adhering the device to an animal using an adhesive.

17. The method of claim 16, further comprising:
- providing the device with another deterrent composition comprising an odor causing composition applied to the solids-permeable membrane; and
- permitting the animal to inhale volatile constituents of the odor causing composition.

* * * * *